United States Patent [19]

Tomalia et al.

[11] Patent Number: 4,631,337
[45] Date of Patent: Dec. 23, 1986

[54] HYDROLYTICALLY-STABLE DENSE STAR POLYAMINE

[75] Inventors: Donald A. Tomalia, Midland; James R. Dewald, Bay City, both of Mich.

[73] Assignee: The Dow Chemical Company, Midland, Mich.

[21] Appl. No.: 755,259

[22] Filed: Jul. 15, 1985

Related U.S. Application Data

[63] Continuation-in-part of Ser. No. 641,807, Aug. 17, 1984, Pat. No. 4,568,737, which is a continuation-in-part of Ser. No. 565,686, Dec. 27, 1983, Pat. No. 4,558,120, and a continuation-in-part of Ser. No. 456,226, Jan. 1, 1983, Pat. No. 4,507,466.

[51] Int. Cl.$^4$ ............................................. C08G 73/00
[52] U.S. Cl. .................................... 528/391; 210/735; 528/423; 528/424; 564/512
[58] Field of Search ........................ 528/391, 423, 424; 564/512; 210/735

[56] References Cited

U.S. PATENT DOCUMENTS 4,507,466  3/1985  Tomalia et al. ...................... 528/363

Primary Examiner—Harold D. Anderson

[57] ABSTRACT

Dense star polyamines having terminal group densities greater than extended conventional star polyamines exhibit greater and more uniform reactivity than their corresponding extended conventional star polyamines. For example, a second generation, amine-terminated polyamine dense star polyamine prepared from tri(2-aminoethyl)amine and aziridine has $4.7 \times 10^{-3}$ amine moieties per unit volume (cubic Angstrom units) in contrast to the $1.7 \times 10^{-3}$ amine moieties per unit volume contained by an extended conventional star polyamine. Such dense star polyamines are useful as calibration standards, high efficiency proton scavengers and in making size selective membranes.

21 Claims, No Drawings

HYDROLYTICALLY-STABLE DENSE STAR POLYAMINE

CROSS-REFERENCE TO RELATED APPLICATIONS

This application is a continuation-in-part of application Ser. No. 641,807, filed on Aug. 17, 1984, now U.S. Pat. No. 4,568,737, which is a continuation-in-part of application Ser. No. 456,226, filed on Jan. 1, 1983, now U.S. Pat. No. 4,507,466, and a continuation-in-part of application Ser. No. 565,686, filed on Dec. 27, 1983, now U.S. Pat. No. 4,558,120.

BACKGROUND OF THE INVENTION

This invention relates to a novel class of branched polyamines containing dendritic branches having functional groups uniformly distributed on the periphery of such branches. This invention also relates to processes for preparing such polyamines as well as applications therefore.

Organic polymers are generally classified in a structural sense as either linear or branched. In the case of linear polymers, the repeating units (often called mers) are divalent and are connected one to another in a linear sequence. In the case of branched polymers, at least some of the mers possess a valency greater than 2 such that the mers are connected in a nonlinear sequence. The term "branching" usually implies that the individual molecular units of the branches are discrete from the polymer backbone, yet have the same chemical constitution as the polymer backbone. Thus, regularly repeating side groups which are inherent in the monomer structure and/or are of different chemical constitution than the polymer backbone are not considered as branches, e.g., dependent methyl groups of linear polypropylene. To produce a branched polymer, it is necessary to employ an initiator, a monomer, or both that possess at least three moieties that function in the polymerization reaction. Such monomer or initiators are often called polyfunctional. The simplest branched polymers are the chain branched polymers wherein a linear backbone bears one or more essentially linear pendant groups. This simple form of branching, often called comb branching, may be regular wherein the branches are uniformly and regularly distributed on the polymer backbone or irregular wherein the branches are distributed in nonuniform or random fashion on the polymer backbone. See T. A. Orofino, *Polymer* 2, 295-314 (1961). An example of regular comb branching is a comb branched polystyrene as described by T. Altores et al. in *J. Polymer Sci., Part A*, Vol. 3, 4131-4151 (1965) and an example of irregular comb branching is illustrated by graft copolymers as described by Sorenson et al. in "Preparative Methods of Polymer Chemistry", 2nd Ed., Interscience Publishers, 213-214 (1968).

Another type of branching is exemplified by cross-linked or network polymers wherein the polymer chains are connected via tetravalent compounds, e.g., polystyrene molecules bridged or cross-linked with divinylbenzene. In this type of branching, many of the individual branches are not linear in that each branch may itself contain groups pendant from a linear chain. More importantly in network branching, each polymer macromolecule (backbone) is cross-linked at two or more sites to two other polymer macromolecules. Also the chemical constitution of the cross-linkages may vary from that of the polymer macromolecules. In this so-called cross-linked or network branched polymer, the various branches or cross-linkages may be structurally similar (called regular cross-linked) or they may be structurally dissimilar (called irregularly cross-linked). An example of regular cross-linked polymers is a ladder-type poly(phenylsilsesquinone) as described by Sorenson et al., supra, at page 390. The foregoing and other types of branched polymers are described by H. G. Elias in *Macromolecules*, Vol. I, Plenum Press, New York (1977).

More recently, there have been developed polymers having so-called star structured branching wherein the individual branches radiate out from a nucleus and there are at least 3 branches per nucleus. Such star branched polymers are illustrated by the polyquaternary compositions described in U.S. Pat. Nos. 4,036,808 and 4,102,827. Star branched polymers prepared from olefins and unsaturated acids are described in U.S. Pat. No. 4,141,847. The star branched polymers offer several advantages over polymers having other types of branching. For example, it is found that the star branched polymers may exhibit higher concentrations of functional groups thus making them more active for their intended purpose. In addition, such star branched polymers are often less sensitive to degradation by shearing which is a very useful property in formulations such as paints, in enhanced oil recovery and other viscosity applications. Additionally, the star branched polymers have relatively low intrinsic viscosities even at high molecular weight.

While the star branched polymers offer many of the aforementioned advantages over polymers having more conventional branching, it is highly desirable to provide polymers which exhibit even greater concentrations of functional groups per unit volume of the polymer macromolecule as well as a more uniform distribution of such functional groups in the exterior regions of the macromolecule. In addition, it is often desirable to provide polymers having macromolecular configurations that are more spheroidal and compact than are the star branched polymers.

SUMMARY OF THE INVENTION

In its broadest aspect, this invention is a hydrolytically-stable dense star polyamine having at least one branch (hereinafter called a core branch) emanating from a core, said branch having at least one terminal group provided that (1) the ratio of terminal groups to the core branches is more than one, preferably two or greater, (2) the density of terminal groups per unit volume in the polyamine is at least 1.5 times that of an extended conventional star polyamine having similar core and monomeric moieties and a comparable molecular weight and number of core branches, each of such branches of the conventional star polyamine bearing only one terminal group, and (3) a molecular volume that is no more than about 80 percent of the molecular volume of said extended conventional star polyamine as determined by dimensional studies using scaled Corey-Pauling molecular models. For purposes of this invention, the term "dense" as it modifies "star polyamine" means that it has a smaller molecular volume than an extended conventional star polyamine having the same molecular weight. The extended conventional star polyamine which is used as the base for comparison with the dense star polyamine is one that has the same molecular weight, same core and monomeric components and same number of core branches as the dense star polyamine. By "extended" is meant that the individual branches of the conventional star polymer are extended or stretched to their maximum length, e.g., as such branches exist when the star polymer is completely solvated in an ideal solvent for the star polymer. In addition while the number of terminal groups, usually amine groups, is greater for the dense star polyamine molecule than in the conventional star polyamine molecule, the chemical structure of the terminal groups is the same.

In a somewhat more limited and preferred aspect, this invention is a polyamine having a novel ordered star branched structure (herein called starburst structure). Hereinafter this polyamine having a starburst structure is called a dendrimer. Thus, a "dendrimer" is a polyamine having a polyvalent core that is covalently bonded to at least two ordered dendritic (tree-like) branches which extend through at least two generations. As an illustration, an ordered second generation dendritic branch is depicted by the following configuration:

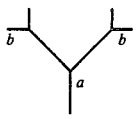

wherein "a" represents the first generation and "b" represents the second generation. An ordered, third generation dendritic branch is depicted by the following configuration:

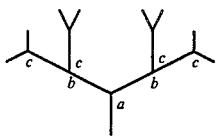

wherein "a" and "b" represent the first and second generation, respectively, and "c" represents the third generation. A primary characteristic of the ordered dendritic branch which distinguishes it from conventional branches of conventional polyamines is the uniform or essentially symmetrical character of the branches as is shown in the foregoing illustrations. In addition, with each new generation, the number of terminal groups on the dendritic branch is an exact multiple of the number of terminal groups in the previous generation.

Another aspect of this invention is a partially protected reactant process for producing the dense star polyamine comprising the steps of (A) contacting (1) a core compound having at least one primary amino moiety (—NH$_2$) or secondary

(—NH)

amine moiety with (2) an N-substituted aziridine having an aziridine moiety which is reactive with the amine moieties of the core compound and (b) a blocking moiety (which is the N-substituent and does not react with the amine moieties of the core) under conditions sufficient to form a blocked core adduct wherein each amine moiety of the core compound has reacted with the aziridine moiety of a different molecule of the N-substituted aziridine to form blocked amine moieties;

(B) removing the blocking moieties from the blocked core adduct to form a first generation adduct;

(C) contacting (1) the first generation adduct which has at least twice the number of terminal amine moieties as the core compound with (2) a N-substituted aziridine having an aziridine moiety which will react with the terminal amine moieties of the first generation adduct and a blocking moiety (which is N-substituted and does not react with the amine moieties of the first generation adduct) under conditions sufficient to form a blocked second generation adduct having a number of blocked amine moieties that are at least twice the number of blocked amine moieties in the blocked core adduct; and (D) removing the blocking moieties from the blocked second generation adduct to form a second generation adduct or dendrimer.

In the foregoing process, the N-substituted aziridines used in the formation of the first and second generation dendrimers may be the same or different. The third and higher generation dendrimers are formed by repeating steps (C) and (D) of the aforementioned process, provided that such generations are not prevented by excessive dense surface packing of the terminal groups in such additional generations. By "dense surface packing", it is meant that the concentration of reactive moieties on the surface of the dense star polyamine is so high that further reaction on a stoichiometric basis is prevented.

Other aspects of this invention are methods for using the dense star polyamines in such applications as size selective membrane and as high efficiency proton scavengers and calibration standards for electron microscopy.

The dense star polyamines of the present invention exhibit the following properties which are unique or are superior to similar properties of extended conventional star branched polyamines and other branched polyamines having similar molecular weight and terminal groups:

(a) greater branch density;
(b) greater terminal group density;
(c) greater accessibility of terminal groups to chemically reactive species; and
(d) lower viscosity.

DETAILED DESCRIPTION OF ILLUSTRATIVE EMBODIMENTS

In the dense star polyamines of the present invention, the core is covalently bonded to at least one core branch, preferably at least two, most preferably at least three, core branches with each core branch having a calculated length of at least 3 Angstrom units (Å), preferably at least 4 Å, most preferably at least 6 Å. These polymers preferably have an average of at least 2, more preferably at least 3 and most preferably at least 4 terminal groups per polyamine molecule. Preferably, the core branches have a dendritic character, most preferably an ordered dendritic character as defined hereinafter.

The dense star polyamines of this invention are preferably dendrimers having two-dimensional molecular diameters in the range from about 12 to about 2000 Angstrom units (Å), more preferably from about 25 to about 500 Å and most preferably from about 50 to about 250 Å. For the purposes of this invention, a two-dimensional molecular diameter is determined by the following electron microscopic method. First, the terminal amine groups of dendrimers are connected to anionic moieties, e.g., carboxylic moieties. This is accomplished by exhaustively reacting the terminal amine groups with methyl acrylate by a Michael addition followed by saponification to carboxylate salts with a stoichiometric amount of sodium hydroxide. A dilute aqueous solution (e.g., about 0.5 weight percent of the dendrimer in water) of the dendrimer is placed on a beryllium grid (~1.5 millimeter diameter puddle) and allowed to evaporate. The dendrimer often exhibits dendritic-like crystalline growth during the evaporation process. The diameter of the dry dendrimer molecules in two-dimensional state are then measured by electron microscopy and found to correspond closely, e.g., within 15 percent, to the diameters predicted by scaled Corey-Pauling molecular models. Such measurements are readily made using a JEM-1200 EX Electron Microscope sold by JEOL Corporation using CTEM techniques on a beryllium grid coated with 50 Å carbon.

The dense star polyamines of this invention preferably have two-dimensional molecular diameters in the range from about 6 to about 1000, more preferably from about 10 to about 250, most preferably from about 25 to about 125, Angstrom units. For the purposes of this invention, a three-dimensional molecular diameter is determined by calculating hydrodynamic diameters using the following Hester-Mitchell relationship, R. D. Hester et al., *J. Poly Sci.*, Vol. 18, p. 1727 (1980).

$$d = \left[\frac{240}{\pi N}\right]^{\frac{1}{3}} [M(\eta)]^{\frac{1}{3}}$$

wherein d is the hydrodynamic diameter in Angstrom units; N is $6.02 \times 10^{23}$; M is number average molecular weight of the dendrimer; $\pi$ is 3.14; and $\eta$ is intrinsic viscosity of the dense star polyamide in deciliters per gram at 25° C.

In dense star polyamines, the terminal groups are amino groups, preferably primary amino groups. While less preferred for many applications, the amino groups may be secondary amino, e.g., methylamino, ethylamino, hydroxyethylamino, benzylamino or mercaptoethylamino; or tertiary amino, e.g., dimethylamino, diethylamino, bis(hydroxyethyl)amino, or other N-alkylated, N-arylated or N-acylated derivatives obtained by reaction with various alkylating agents, arylating agents or acylating agents, respectively. It is further understood that the terminal amino groups of the dense star polyamines may be substituted with other groups using conventional procedures as described in detail hereinafter. The dense star polyamines differ from conventional star or star-branched polyamines in that the dense star polyamines have a greater concentration of terminal groups per unit of molecular volume than do extended conventional star polyamines having an equivalent number of core branches and an equivalent core branch weight. Thus, the density of terminal amino groups per unit volume in the dense star polyamine is at least about 1.5 times the density of terminal groups in the extended conventional star polyamine, preferably at least 5 times, more preferably at least 10 times, most preferably from about 15 to about 50 times. The ratio of terminal groups per core branch in the dense star polyamine is preferably at least 2, more preferably at least 3, most preferably from about 4 to about 1024. Preferably, for a given polyamine molecular weight, the molecular volume of the dense star polyamine is less than 70 volume percent, more preferably from about 16 to about 60, most preferably from about 7 to about 50 volume percent of the molecular volume of the extended conventional star polyamine.

In the preferred dense star polyamines, the density of terminal primary amine moieties in the polyamine is readily expressed as the molar ratio of primary amine moieties to the total of secondary and tertiary amine moieties. In such polymers this 1° amine:(2° amino+3° amine) is preferably from about 0.37:1 to about 1.33:1, more preferably from about 0.69:1 to about 1.2:1, most preferably from about 1.0:1 to about 1.2:1.

The preferred dendrimers of the present invention are characterized as having a polyvalent core that is covalently bonded to at least two ordered dendritic branches which extend through at least two generations. Such ordered branching can be illustrated by the following sequence wherein G indicates the number of generations:

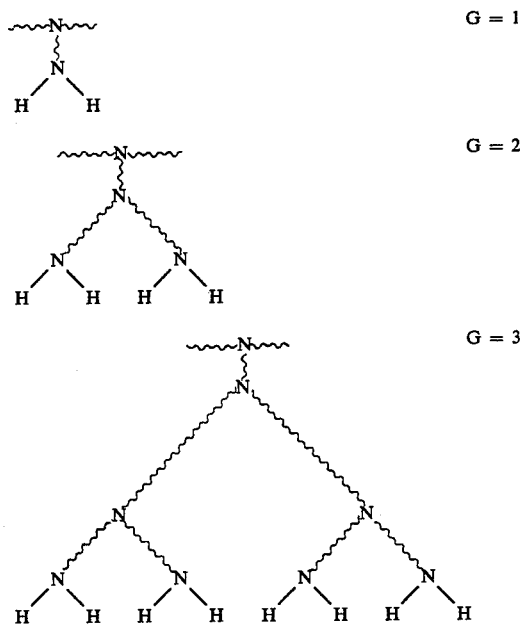

Mathematically, the relationship between the number of terminal groups on a dendritic branch and the number of generations of the branch in a homopolymer dendrimer can be represented as follows:

$$\text{\# of terminal groups per dendritic branch} = \frac{N_r{}^G}{2}$$

wherein G is the number of generations and $N_r$ is the repeating unit multiplicity which is at least 2 as in the case of amines. The total number of terminal groups in the dendrimer is determined by the following:

$$\text{\# of terminal groups per dendrimer} = \frac{N_c N_r{}^G}{2}$$

wherein G and $N_r$ are as defined before and $N_c$ represents the valency (often called core functionality) of the core compound. Accordingly, the homopolymer dendrimers of the present invention can be represented in its component parts as follows:

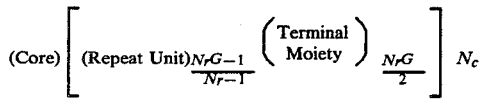

wherein the Core, Terminal Moiety, G and $N_c$ are as defined before and the Repeat Unit has a valency or functionality of $N_r+1$ wherein $N_r$ is as defined before.

A copolymer dendrimer which is preferred for the purposes of this invention is a unique compound constructed of polyfunctional monomer units in a highly branched (dendritic) array. The dendrimer molecule is prepared from a polyfunctional initiator unit (core compound), polyfunctional repeating units and terminal units which may be the same or different from the repeating units. The core compound is represented by the formula $(\text{I})(Z^c)N_c$ wherein $\text{I}$ represents the core, $Z$ represents the functional groups bonded to $\text{I}$ and Nc represents the core functionality which is preferably 2 or more, most preferably 3 or more. Thus, the dendrimer molecule comprises a polyfunctional core, $\text{I}$, bonded to a number (Nc) of functional groups, $Z^c$, each of which is connected to the monofunctional tail of a repeating unit, $X^1Y^1(Z^1)_{N1}$, of the first generation and each of the Z groups of the repeating unit of one generation is bonded to a monofunctional tail of a repeating unit of the next generation until the terminal generation is reached. In the dendrimer molecule, the repeating units are the same within a single generation, but may differ from generation to generation. In the repeating unit, $X^1Y^1(Z^1)_{N1}$, $X^1$ represents the monofunctional tail of the first generation repeating unit, $Y^1$ represents the moiety constituting the first generation, $Z^1$ represents the functional group of the polyfunctional head of the repeating unit of the first generation and may be the same as or different from the functional groups of the core compound, $\text{I}(Z)_{Nc}$, or other generations; and $N^1$ is a number of 2 or more, most preferably 2, 3 or 4, which represents the multiplicity of the polyfunctional head of the repeating unit in the first generation. Generically, the repeating unit is represented by the formula $X^iY^i(Z^i)_{Ni}$ wherein "i" represents the particular generation from the first to the $t-1$ generation. Thus, in the preferred dendrimer molecule, each $Z^1$ of the first generation repeating unit is connected to an $X^2$ of a repeating unit of the second generation and so on through the generations such that each $Z^i$ group for a repeating unit $X^iY^i(Z^i)_{Ni}$ in generation number "i" is connected to the tail $(X^{i+1})$ of the repeating unit of the generation number "i+1". The final or terminal generation of a preferred dendrimer molecule comprises terminal units, $X^tY^t(Z^t)_{Nt}$ wherein t represents terminal generation and corresponds to the total number of generations and $X^t$, $Y^t$, $Z^t$ and $N^t$ may be the same as or different from $X^i$, $Y^i$, $Z^i$ and $N^i$ except that there is no succeeding generation connected to the $Z^t$ groups and $N^t$ may be less than two, e.g., zero or one. Therefore the preferred dendrimer has a molecular formula represented by

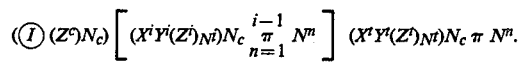

for $i = 0$ to $t - 1$ wherein the symbols are as previously defined. The $\pi$ function is the product of all the values between its defined limits. Thus $$\pi_{n=1}^{i-1} N^n = (N^1)(N^2)(N^3)(N^{i-2})(N^{i-1})$$

which is the number of repeat units, $X^iY^i(Z^i)_{Ni}$, comprising the ith generation of one dendritic branch. In copolymer dendrimers, the repeat unit for one generation differs from the repeat unit in at least one other generation. The preferred dendrimers are very symmetrical as illustrated in structural formulas described hereinafter. Preferred dendrimers may be converted to functionalized dendrimers by contact with another reagent. For example, conversion of primary amines in the terminal generation to amides by reaction with an acid chloride gives an amide terminally functionalized dendrimer. Quaternization of the internal tertiary amines by contact with dimethyl sulfate gives a quaternary ammonium internally functionalized dendrimers. The dendrimers may be functionalized terminally, internally, or both. This functionalization need not be carried out to the theoretical maximum as defined by the number of available functional groups and, thus, a functionalized dendrimer may not have high symmetry or a precisely defined molecular formula as is the case with the present dendrimer.

An illustration of a functionally active dendrimer of a ternary or trivalent core which has three ordered, second generation dendritic branches is depicted by the following configuration:

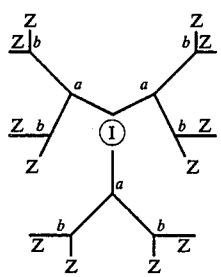

wherein "$\text{I}$" is a trivalent core atom or molecule having a covalent bond with each of the three dendritic branches, "Z" is a terminal amine moiety and "a" and "b" are as defined hereinbefore. An example of such a ternary dendrimer is polyamine represented by the following structural formula:

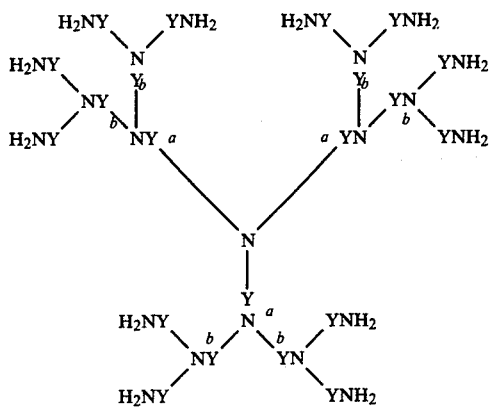

wherein Y represents a divalent alkylene moiety such as ethylene (—CH$_2$CH$_2$—), propylene (—CH$_2$CH$_2$CH$_2$— or —CH$_2$CHCH$_3$) and other alkylenes having from 4 to 6 carbons and alkyleneamino, alkyleneaminoalkylene and polyalkylenepolyamine, and "a" and "b" indicate first and second generations, respectively. In these two illustrations, $N_c$ is 3 and $N_r$ is 2. In the latter of the two illustrations, the Repeat Unit is YN. While the foregoing configuration and formula illustrate a trivalent core, the core atom or molecule may be any monovalent or monofunctional moiety or any polyvalent or polyfunctional moiety, preferably a polyvalent or polyfunctional moiety having from 2 to about 2300 valence bonds or functional sites available for bonding with the dendritic branches, most preferably from about 3 to about 200 valence bonds or functional sites. In cases wherein the core is a monovalent or monofunctional moiety, the dense star polyamine has only one core branch and must be compared with a linear polyamine in order to determine appropriate terminal group density and molecular volume. Accordingly, this dense star polyamine must have at least 2 generations in order to exhibit the desired density of terminal groups. Also, Y may be any other divalent organic moiety such as arylene (e.g., phenylene), arylenealkylene, alkylenearylenealkylene, alkyleneoxy (e.g., ethyleneoxy), and the like, with the depicted alkylene moiety being more preferred and ethylene being the most preferred. It is further understood that Y may be a polyvalent moiety such as triyls, tetrayls and other polyyls of aliphatic and aromatic hydrocarbons, e.g.,

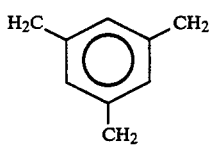, 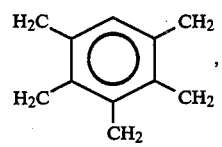,

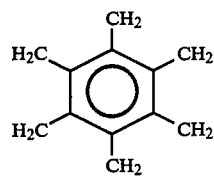

and the like. In addition to amine, the terminal groups of the dendrimer may be any functionally active moiety that can be used to propagate the dendritic branch to the next generation. Examples of such other moieties include ester moieties such as alkoxycarbonyl, ethylenically unsaturated moieties such as alkenyl, aziridinyl, oxazolinyl, haloalkyl, oxiranyl, mercapto, hydroxy, isothiocyanato and isocyanato, with amino moieties being preferred. While the dendrimers preferably comprise dendritic branches having 2 to 6 generations, dendrimers comprising dendritic branches up to 12 generations are suitably made and employed in the practice of this invention.

More preferably, the amine dendimers of this invention are represented by the formula:

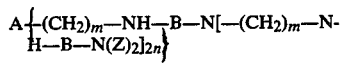

wherein A is an n-valent core derived from ammonia or an amine compound, B is a divalent moiety capable of linking amine groups, m is an integer of 2 to 12, n is an integer of 3 or more corresponding to the number of the core branches and Z is hydrogen, alkyl, aryl, alkylaryl, hydroxyalkyl, mercaptoalkyl, alkoxycarbonyl,

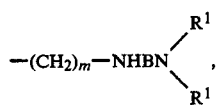

wherein R$^1$ is hydrogen or

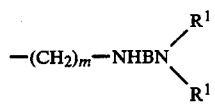

wherein each generation is represented by

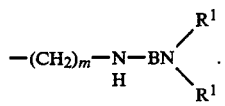

More preferably A is a core such as

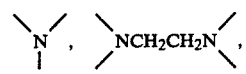

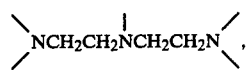

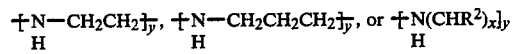

wherein R$^2$ is alkyl or aryl, x is 2 or 3 and y is an integer from 2 to 2300; B is the divalent residue of a polyamine, most preferably an alkylene polyamine such as ethylene diamine or a polyalkylene polyamine such as triethylene tetramine; n is an integer from 3 to 2000, more preferably from 3 to 1000, most preferably from 3 to 125; m is 2 to 12, preferably 2 to 6; and Z is most preferably —(CH$_2$)$_2$NH(CH$_2$)$_n$NH$_2$, —CHR$^2$CH$_2$NH$_2$ wherein R$^2$ is alkyl, —(CH₂)₂NH(CH₂)₂NH(CH₂)₂NH₂ or

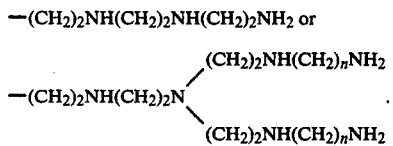

The dense star polyamines of this invention are readily prepared by reacting a compound capable of generating a polyvalent core with a compound or compounds which causes propagation of dendritic branches from the core. The compound capable of generating a polyvalent core, $W(X)_n$, wherein W is the polyvalent core atom and is covalently bonded to nX reactive terminal groups (usually amino and $n \geq 2$), is reacted with a partially protected multifunctional reagent, $T\text{-}(U)\ \textcircled{V}\ _y$, wherein U represents a multivalent moiety covalently bonded to y $\textcircled{V}$ protected moieties ($y \geq 2$), and to one T, a moiety capable of reacting with X to form $W[(X'\text{—}T'\text{)-}U\ \textcircled{V}\ _y]_n$, wherein X' and T' represent the residue of reaction between X and T. This first generation compound is then subjected to activation conditions whereby the $\textcircled{V}$ moieties are made reactive (deprotected) and reacted with the partially protected multifunctional reagent, $T\text{—}U\text{—}\ \textcircled{V}\ _y$, to form the second generation protected dendrimer, $W[\text{-}(X'\text{—}T'\text{—}U\ \textcircled{V}\ )_y T'\text{)-}U\ \textcircled{V}\ _y]_n$. This protected dendrimer can be activated and reacted again in a similar manner to provide the third generation protected dendrimer. This partially protected reactant method is specifically illustrated hereinafter.

Illustrative of the partially protected reactant method, dense star polyamines including polyamine dendrimers may be prepared by reacting ammonia or an amine having a plurality of primary amine groups with N-substituted aziridine such as N-tosyl aziridine,

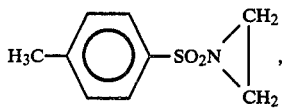

N-methanesulfonyl aziridine, N-trifluoromethanesulfonyl aziridine; N-acyl aziridines such as

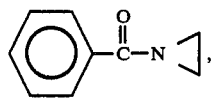

and the corresponding azetidine derivatives, e.g.,

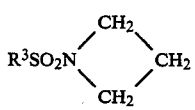

wherein $R^3$ is alkyl such as methyl, ethyl and propyl; aryl such as phenyl; and polyfluoroalkyl such as trifluoromethyl or other perfluoroalkyl, to form a protected first generation polysulfonamide. This product is then activated with acid such as hydrochloric or sulfuric acid to form the first generation polyamine salt, neutralized with sodium hydroxide and then reacted with further N-tosyl aziridine to form the protected second generation polysulfonamide which sequence can be repeated to produce higher generation polyamines using the general reaction conditions described in Humrichause, C. P., PhD, Thesis from University of Pennsylvania, "N-Substituted Aziridines as Alkylating Agents", Ref. No. 66-10, 624 (1966).

In the foregoing method of dense star polyamine preparation, water or hydrogen sulfide may be employed as nucleophilic cores for the production of binary dendrimers. Examples of other nucleophilic core compounds include phosphine, polyalkylene polyamines such as diethylenetriamine, triethylenetetramine, tetraethylenepentamine and both linear and branched polyethylenimine; primary amines such as methylamine, hydroxyethylamine, octadecylamine and polymethylenediamines such as hexamethylenediamine; polyaminoalkylarenes such as 1,3,5-tris(aminomethyl)-benzene; tris(aminoalkyl)amines such as tris(aminoethyl)amine; heterocyclic amines such as imidazolines and piperidines; and various other amines such as hydroxyethylaminoethylamine, mercaptoethylamine, morpholine, piperazine, amino derivatives of polyvinylbenzyl chloride and other benzylic polyamines such as tris(1,3,5-aminomethyl)benzene. Other suitable nucleophilic cores include polyols such as the aforementioned pentaerythritol, ethylene glycol and polyalkylene polyols such as polyethylene glycol and polypropylene glycol; 1,2-dimercaptoethane and polyalkylene polymercaptans; thiophenols, and phenols. Of the core compounds, ammonia, alkylene diamines and the polyalkylene polyamines are preferred for the preparation of polyamine dendrimers and other dense star polyamines by this method. Also preferred as core compounds are the star/comb-branched polyamines described in U.S. patent application Ser. No. 683,299, filed Dec. 14, 1984, which is hereby incorporated by reference in its entirety.

Examples of N-substituted aziridines suitably employed in this invention include N-tosyl aziridine, N-methanesulfonyl aziridine, N-trifluoromethanesulfonyl aziridine, N-benzoyl aziridine and the like. Examples of suitable N-substituted azetidines include N-tosyl azetidine, N-methanesulfonyl azetidine, N-trifluoromethanesulfonyl azetidine and the like.

Thus prepared, the polyamine dendrimers and other dense star polyamines can be reacted with a wide variety of compounds hereinafter collectively referred to as a reagent capable of reacting with the amine moieties of the polyamine to produce the polyfunctional compounds having the unique characteristics that are attributable to the structure of the dendrimer. For example, a dendrimer having terminal amine moieties, may be reacted with an unsaturated nitrile to yield a polynitrile (nitrile-terminated) dendrimer. Alternatively, the polyamine dendrimer may be reacted with (1) an $\alpha,\beta$-ethylenically unsaturated amide to form a polyamide (amide-terminated) dendrimer, (2) an $\alpha,\beta$-ethylenically unsaturated ester to form a polyester (ester-terminated) dendrimer, (3) an ethylenically unsaturated sulfide to yield a polymercapto (thiol-terminated) dendrimer, or (4) an alkylene oxide to produce a hydroxy-terminated dendrimer and, optionally then with thionyl chloride to form a chloro-terminated dendrimer or with a tosylate to form a tosyl-terminated dendrimer. The tosyl- and chloro-terminated dendrimers are examples of electrophile-terminated dendrimers. The chloro-terminated dendrimer can be reacted with trialkyl sodiomethane tricarboxylate to form tricarboxyester-terminated dendrimers. An ester (alkoxycarbonyl)-terminated dendrimer such as (2) above or derived from halocarboxylic acid, can be reacted with alkanolamines such as diethanolamine, aminoethylethanolamine, or tris(hydroxymethyl)aminoethane to produce hydroxy-terminated dendrimers.

In addition, the dendrimer may be reacted with an appropriate difunctional or trifunctional compound such as an organo polyhalide, e.g., 1,4-dichlorobutane; polyesters such as poly(methyl acrylate); polyethers such as polyepichlorohydrin or polyisocyanate or polyisothiocyanate such as toluene diisocyanate, methylene diphenylene diisocyanate and polymers thereof (so-called MDI and polymeric MDI) and other aromatic polyisocyanates, aliphatic polyisocyanates, and polyisothiocyanates corresponding to the aforementioned polyisocyanates, to form a poly(dendrimer) or bridged dendrimer having a plurality of dendrimers linked together through the residues of the polyhalide, polyester, polyether or polyisocyanate. The bridged dendrimers can also be prepared by combining stoichiometric amounts of amine-terminated dendrimers of this invention with ester-terminated dendrimers of this invention or those described in U.S. Pat. No. 4,507,466. Dendrimer bridging also results when amine-terminated dendrimer is mixed with aziridine-terminated dendrimer under reaction conditions.

Such reactions are further exemplified by the following working examples. In such working examples, all parts and percentages are by weight unless otherwise indicated.

EXAMPLE 1

A. Preparation of First Generation Dense Star Polymer

A 35.5 percent solution of $H_2SO_4$ in $H_2O$ is made by dissolving 191.1 g ($H_2SO_4$, 98 percent) in 347 g of deionized water. To this solution, in a 500-ml 3-necked flask equipped with stirrer, condenser and addition funnel, is added neat diethylenetriamine (154.5 g, 1.5 moles), while stirring and cooling (ice) at such a rate that the temperature does not exceed 65° C.–70° C. After this addition, aziridine (21.5 g, 0.5 mole) is added dropwise while stirring and cooling (<50°) over a period of 0.5 hour. The resulting bright yellow, orange reaction mixture is then stirred while heating at 40° C.–50° C. for 6 hours. To this crude reaction mixture is added 240 g (6.0 moles) of NaOH in portions while stirring. An exotherm is noted which gives a brown-yellow layer which separates from a lower, salt-containing, aqueous layer. The organic (top) layer is separated and found to weigh 287.3 g and contains a substantial amount of water. Solid sodium hydroxide (75 g) is added to this fraction causing a brown layer (top) to separate, which weighs 174.3 g (99 percent of theory). Distillation through a ½×8 inch Vigreux column gives a light yellow liquid, b.p. 123° C.–128° C. at 3 mm Hg, which is determined to be the adduct of 1 mole of aziridine and 1 mole of diethylenetriamine represented by the formula:

B. Preparation of N-(Tosyl)Aziridine p-Toluene sulfonyl chloride (38.0 g, 0.2 mole) is dissolved in 100 ml of diethyl ether in a 250-ml 3-necked flask equipped with stirrer, condenser and addition funnel. To this stirred solution is added triethylamine (20.2 g, 0.2 mole) in a dropwise manner. While stirring and maintaining the reaction temperature at 10° C.–20° C. with an ice-bath, a solution of aziridine (8.6 g, 0.2 mole) in 75 ml of diethyl ether is added dropwise over a period of 15–30 minutes. A thick white precipitate forms. Additional ether (100–150 ml) may be added to facilitate stirring. The reaction mixture is stirred for an additional hour at room temperature and filtered. Washing the filter cake with 2×100 ml portions of ether gives essentially a quantitative yield of $Et_3N.HCl$. Removal of solvent from the filtrate gives light cream colored crystals which weigh 25.0 g (62 percent yield). Recrystallization from $Et_2O$/hexane gives white crystals, m.p. 60° C.–62° C. which are determined by nuclear magnetic resonance to be N-(tosyl)aziridine represented by the formula:

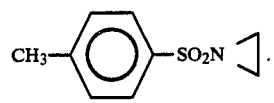

C. Preparation of Protected Polyamine Dendrimer (Second Generation)

The first generation polyamine of Part A (3.5 g, 0.024 mole) and N-tosyl (TOS) aziridine (28.55 g, 0.145 mole) are placed in 50 ml of 95 percent ethanol in a 100-ml vessel equipped with a stirrer. The mixture is stirred at room temperature. Over a period of 2 hours the tosyl aziridine slowly dissolves giving a colorless homogeneous solution after which a white precipitate forms which makes stirring difficult. Additional stirring (1 hour) leads to a solid mass. After adding another 50 ml of ethanol and stirring overnight (25° C.), the white solids are isolated by filtration, washed with 2×100 ml EtOH and 2×150 ml $Et_2O$ and dried by suction. Weight of white solids product is 27.7 g (87 percent). Nuclear magnetic resonance spectral analysis confirms the tosyl hexaadduct represented by the formula:

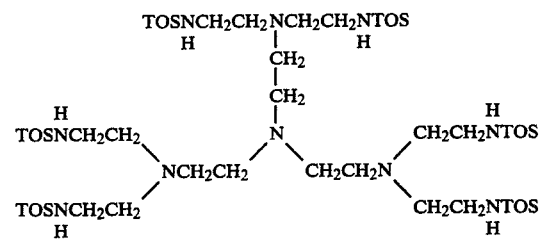

D. Removal of Protecting Tosyl Groups

The protected polyamine dendrimer of Part C (27.7 g, 0.021 mole) is mixed with 130 ml of degassed concentrated sulfuric acid (98 percent) under nitrogen in a one-liter round-bottom flask equipped with stirrer, nitrogen purge and reflux condenser. The mixture is heated at 130° C. for 6 hours. The reaction is complete after 6–10 hours as determined by a test which involves basifying the sample with 10 percent NaOH. The absence of cloudiness at alkaline pH indicates complete reaction. After cooling the reaction mixture to 0° C., diethyl ether (600 ml) is added in small portions to maintain the temperature ≦10° C. The resulting white, hygroscopic precipitate is isolated by filtration and then dissolved in water. This water solution is basified to pH≧10 with 20 percent KOH. Removal of the water yields a mixture of oily product and solid $K_2SO_4$. Extraction with methanol (200 ml) and filtration gives the product as a flowable oil, after methanol removal. Upon heating under high vacuum, the remaining volatiles are removed to give a yellow-orange syrup. Nuclear magnetic resonance spectral analysis confirms the aforementioned syrup to be a second generation polyamine dendrimer represented by the formula:

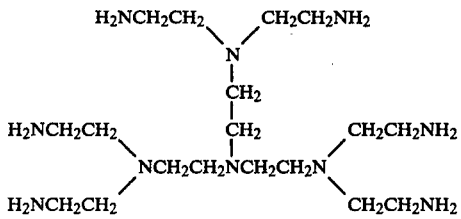

EXAMPLE 2

A. Preparation of Protected Polyamine Dendrimer (Third Generation)

A 37.85-g (0.192 mole) portion of tosyl aziridine and 200 ml of ethanol (100 percent) are stirred at 25° C. in a one-liter flask for ½ hour. To this stirred mixture is added 6.31 g of the second generation polyamine dendrimer of Example 1. The solids dissolve within one hour, and the resulting solution is stirred for 12 hours at 25° C. The reaction mixture in the form of a pale yellow syrup is stripped of ethanol to yield 44.17 g of the tosyl derivative (sulfonamide) of the second generation polyamine dendrimer.

B. Removal of Protecting Tosyl Groups

The tosyl derivative (44.17 g) and 140 ml of concentrated sulfuric acid (98 percent) are placed in a one-liter flask while bubbling $N_2$ through the resulting solution. The solution is heated at 130° C. for 6 hours and then cooled in a dry ice bath. A 600-ml portion of diethyl ether is added to the solution at a rate sufficient to maintain the solution temperature below $-10°$ C. The resulting dark precipitate is filtered and then dissolved in 200 ml of deionized water. The pH of the solution is increased to 10 by adding NaOH (50 percent) and water is removed under vacuum. The resulting product is extracted with 200 ml of methanol and the methanol is stripped leaving a black viscous oil. The product is dried, dissolved in 200 ml of toluene at reflux temperature. The toluene is then stripped leaving 7.6 g of a yellow oil which is determined to be a third generation polyamine dendrimer represented by the formula:

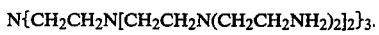

N{CH2CH2N[CH2CH2N(CH2CH2NH2)2]2}3.

EXAMPLE 3

A. Transition Metal Ion Control

A 0.1-g portion of the polyamine dendrimer of Part D of Example 1 dissolved in 5 ml of deionized water is added dropwise under ambient conditions to a solution of 0.1 g of copper sulfate in 3 ml of deionized water. A deep blue color accompanied by the formation of a heavy precipitate (floc) is observed. The precipitate is readily removed by centrifugation, thus demonstrating the control (removal) of Cu (II) ion by formation of complex between Cu (II) ion and dendrimer.

B. Heavy Metal Ion Control

A 0.1-g portion of the polyamine dendrimer of Part D of Example 1 dissolved in 5 ml of deionized water is added dropwise under ambient conditions to a solution of 0.1 g of uranyl nitrate (UO2(NO3)2.6H2O) dissolved in 3 ml of deionized water. A brilliant yellow color accompanied by the formation of a heavy precipitate (floc) is observed. The resulting complex (precipitate) is isolated by centrifugation, thus demonstrating the ability of dendrimer to control (remove) U (VI) ion formation of complex between the dendrimer and the U (VI) ion.

What is claimed is:

1. A dense star polyamine having at least one core branch emanating from a core, each core branch having at least one terminal amine group provided that (1) the ratio of terminal amine groups to the branches emanating from the core is 2:1 or greater, (2) the density of terminal amine groups in the dense star polyamine is at least 1.5 times that of an extended conventional star polyamine having similar core and monomeric moieties and a comparable molecular weight and number of core branches wherein each of such branches of the conventional star polyamine bears only one terminal amine group, and (3) a molecular volume that is equal to or less than 80 percent of the molecular volume of said extended conventional star polyamine.

2. The dense star polyamine of claim 1 wherein the two-dimensional molecular diameter of the dense star polyamine is in the range from about 12 to about 2000 Angstrom units.

3. The dense star polyamine of claim 2 having (1) at least 2 core branches per core, (2) a terminal amine group density at least 5 times that of the corresponding extended conventional star polyamine, (3) a molecular volume that is equal to or less than 50 percent of the volume of the extended conventional star polyamine, and (4) the two-dimensional molecular diameter of the dense star polyamine is in the range from about 25 to about 500 Angstrom units.

4. The dense star polyamine of claim 1 having at least 3 core branches per core.

5. The dense star polyamine of claim 3 having at least 3 core branches per core.

6. The dense star polyamine which is a dendrimer represented by the formula:

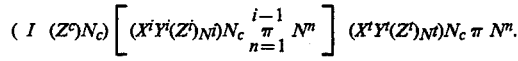

for $i = 0$ to $t - 1$ wherein I is a polyfunctional core, $Z_c$ is a functional group bonded to the core and an X group of the first generation, $N_c$ is the number of functional group bonded to the core, $X^i$ is a monofunctional tail of a repeating unit $Y^i$ of the i generation which is bonded to $Y^i$ and a Z group of the $i-1$ generation, $Z^i$ is a functional group bonded to $Y^i$ and an X group of the $i+1$ generation, $N^i$ is a number of at least 2 which corresponds to the multiplicity of the polyfunctional head of $Y^i$, $\pi$ is the product function, $N^{i-1}$ is a number of at least 2 which corresponds to the multiplicity of the polyfunctional head of $Y^{i-1}$ wherein $Y^{i-1}$ is a repeating unit of the $Y^{i-1}$ generation, $X^t$ is the monofunctional tail of a repeating unit $Y^t$ of the terminal generation, $Z^t$ is a terminating group bonded to $Y^t$, $N^t$ is zero or a number which corresponds to the number of $Z^t$ groups bonded to one $Y^t$ group, i represents a nunmber of a particular generation in a series from 1 to a number from 1 to $t-1$, provided that (1) all $X^iY^i(Z^i)_{Ni}$ are the same within a generation and may be the same or different in different generations and (2) all $X^rY^t(Z^t)_{Nt}$ of the terminal generation are the same.

7. The dense star polyamine of claim 6 wherein t is 2 or more and $N^t$ is at least one.

8. The dense star polyamine of claim 6 wherein t is 3 or more and $N_t$ is at least two.

9. A functionalized dendrimer which is the reaction product of the dense star polyamine of claim 6 and a reagent capable of reacting with the amine moieties of said polyamine, said reagent selected from the group consisting of unsaturated nitrile, α,β-ethylenically unsaturated sulfide, or alkylene oxide.

10. The dendrimer of claim 9 wherein the amine moieties that react with the reagent are internal amine moieties.

11. The dendrimer of claim 9 wherein the amine moieties that react with the reagent are terminal amine moieties.

12. The dendrimer of claim 9 wherein both terminal and internal amine moieties react with the reagent.

13. The polyamine of claim 1 which is a dendrimer having a polyvalent core that is covalently bonded to at least 1 ordered dendritic branch which extends to two generations such that each dendritic branch has at least four terminal groups and a symmetrical structure.

14. The polyamine of claim 1 wherein the dendritic branches contain amine linkages.

15. The polyamine of claim 6 wherein the core is derived from a nucleophilic compound and the branches are polyalkylene polyamines wherein the terminal groups are primary amine groups.

16. The polyamine of claim 6 wherein the nucleophilic core is derived from a core compound having a plurality of active hydrogens capable of reacting with an aziridine or azetidine.

17. The polyamine of claim 15 wherein the nucleophilic compound is an amine having a plurality of amine hydrogens.

18. The polyamine of claim 15 wherein the branches are polyalkylene polyamine, which is derived from the reaction of an aziridine or azetidine with an alkylene polyamine or a polyalkylene polyamine.

19. The polyamine of claim 1 which is represented by the structural formula:

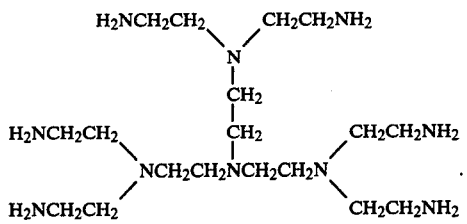

20. The polyamine of claim 6 which is represented by the structural formula:

N{CH$_2$CH$_2$N[CH$_2$CH$_2$N(CH$_2$CH$_2$NH$_2$)$_2$]$_2$}$_3$.

21. A process for producing a dense star polyamine of claim 1 comprising the steps of
(A) contacting
  (1) a core compound having at least one primary amino moiety (—NH$_2$) or secondary

(—NH)

amine moiety with
  (2) an N-substituted aziridine having an aziridine moiety which is reactive with the amine moieties of the core compound and (b) a blocking moiety (which is the N-substituent and does not react with the amine moieties of the core) under conditions sufficient to form a blocked core adduct wherein each amine moiety of the core compound has reacted with the aziridine moiety of a different molecule of the N-substituted aziridine to form blocked amine moieties;
(B) removing the blocking moieties from the blocked core adduct to form a first generation adduct;
(C) contacting
  (1) the first generation adduct which has at least twice the number of terminal amine moieties as the core compound with
  (2) a N-substituted aziridine having an aziridine moiety which will react with the terminal amine moieties of the first generation adduct and a blocking moiety (which is N-substituted and does not react with the amine moieties of the first generation adduct) under conditions sufficient to form a blocked second generation adduct having a number of blocked amine moieties that are at least twice the number of blocked amine moieties in the blocked core adduct; and
(D) removing the blocking moieties from the blocked second generation adduct to form a second generation adduct or dendrimer.

* * * * *

UNITED STATES PATENT AND TRADEMARK OFFICE
CERTIFICATE OF CORRECTION

PATENT NO. : 4,631,337
DATED : December 23, 1986
INVENTOR(S) : Donald A. Tomalia and James R. Dewald It is certified that error appears in the above-identified patent and that said Letters Patent is hereby corrected as shown below:

Column 1, line 3, the word "POLYAMINE" should read --POLYAMINES--

Column 1, line 49, the word "Polymer" should read -- Polymer, --

Column 4, line 38, "membrane" should be -- membranes --.

Column 5, line 43, "polyamide" should be -- polyamine --.

Column 13, line 62, the caption -- First Generation Dense Star Polymer-- should be inserted under the formula shown on lines 60-61.

Column 15, line 17, the caption -- Polyamine Dendrimer (Second Generation) -- should be inserted under the formula shown on lines 9-16.

Column 16, line 40, the word "The" should be -- A -- in Claim 6.

Column 16, line 45, the symbol "I" in the formula should be --Ⓘ--.

Column 16, line 49, the symbol "I" should appear --Ⓘ--.

Column 16, line 65, the word "nunmber" should be -- number --.

Signed and Sealed this

Twenty-fourth Day of May, 1994

*Attest:*

BRUCE LEHMAN

*Attesting Officer*    *Commissioner of Patents and Trademarks*